United States Patent [19]

Kita et al.

[11] Patent Number: 5,556,991
[45] Date of Patent: Sep. 17, 1996

[54] MALEIMIDE COMPOUNDS HAVING IMPROVED IN STORAGE STABILITY

[75] Inventors: Yuichi Kita; Koichi Nakagawa; Kazuo Kishino, all of Hyogo, Japan

[73] Assignee: Nippon Shokubai Co., Ltd., Osaka-fu, Japan

[21] Appl. No.: 256,829

[22] PCT Filed: Jan. 29, 1993

[86] PCT No.: PCT/JP93/00112

§ 371 Date: Sep. 22, 1994

§ 102(e) Date: Sep. 22, 1994

[87] PCT Pub. No.: WO93/15048

PCT Pub. Date: Aug. 5, 1993

[30] Foreign Application Priority Data

Jan. 30, 1992  [JP]  Japan ................. 4-015127

[51] Int. Cl.[6] .................. C07D 207/448; C07D 207/452
[52] U.S. Cl. ........................... 548/548; 548/549
[58] Field of Search ............................. 548/549

[56] References Cited

U.S. PATENT DOCUMENTS 4,623,734  11/1986  Kita et al. ................. 207/448
4,851,547   7/1989  Kita et al. ................. 548/548
5,045,233   9/1991  Kita et al. ................. 252/399

FOREIGN PATENT DOCUMENTS

| 45-16941 | 6/1970 | Japan . |
| 50-36454 | 4/1975 | Japan . |
| 60-100554 | 6/1985 | Japan . |
| 60-112759 | 6/1985 | Japan . |
| 62-63561 | 3/1987 | Japan . |
| 62-138468 | 6/1987 | Japan . |
| 4-346973 | 5/1991 | Japan . |

*Primary Examiner*—David B. Springer
*Attorney, Agent, or Firm*—Omri M. Behr, Esq.

[57] ABSTRACT

The present invention provides a stabilized maleimide compound which is hard to discolor during storage. The maleimide compound has a content of primary amines of not more than 500 ppm or further has a content of maleic anhydride in the range of 5 to 2,000 ppm or a content of 2-amino-N-substituted succinimide compounds of not more than 300 ppm. Furthermore, it is preferable that the content of chlorine compounds reduced as a chlorine atom is not more than 10 ppm and further the content of volatile components having a boiling point of not more than 200° C. at normal pressure is not more than 2,000 ppm.

7 Claims, No Drawings ns are varied. Maleimide
MALEIMIDE COMPOUNDS HAVING IMPROVED IN STORAGE STABILITY

TECHNICAL FIELD

The present invention relates to a maleimide compound with improved storage stability which is hard to discolor. More particularly, it relates to a maleimide compound useful as a raw material for producing a heat resistant polymer such as AS resin, ABS resin and the like.

BACKGROUND ART

A maleimide compound is solid or liquid at room temperature so it is stored in various forms. For example, a solid maleimide is handled in the form of tablets, flakes, powders, etc. at room temperature and the forms thereof during storage such as flake container bags, drum containers, gallon containers, paper bags, tank containers are varied. Maleimide compound in heated molten state is stored in storage tanks in a liquid state.

There has been a problem that the color of the maleimide compound is changed gradually to a blown color, and sometimes into a slightly bluish black brown color, when it is stored in such a solid or liquid state. The rate of discoloration of the maleimide compound varies depending on state, form and storage conditions of the stored maleimide compound, and the discoloration of the maleimide compound during its storage is inevitable although it can occur quickly or slowly.

Discoloration of the maleimide compound is an important problem when used. That is, since the maleimide compound itself is a kind of raw monomer used for improving heat resistance of various thermoplastic resins such as styrene type resins, e.g., AS resin and ABS resin, methyl methacrylate resins, and vinyl chloride resins, etc., the discoloration of the maleimide compound makes the various thermoplastic resins discolored, and as a natural result, the commercial value of the thermoplastic resins decreases considerably. Thus it is necessary to solve the discoloration problem just mentioned above.

Accordingly, an object of the present invention is to provide a stabilized maleimide compound which is hard to discolor during its storage.

DISCLOSURE OF INVENTION

The above object can be attained by a maleimide compound with improved storage stability wherein the content of primary amines is not more than 500 ppm.

The above object can also be attained by a maleimide compound with improved storage stability wherein the content of primary amines is not more than 500 ppm and the content of maleic anhydride is in the range of 5 to 2,000 ppm.

The above object can further be attained by a maleimide compound with improved storage stability wherein the content of primary amines is not more than 500 ppm and the content of 2-amino-N-substituted succinimide compounds is not more than 300 ppm.

We have extensively studied about a cause for discoloration of the maleimide compound in order to solve the above-mentioned problem, to find that the discoloration of She maleimide compound is not occurred by the change in the quality of the maleimide compound itself rather than by the presence of the amines contained in the maleimide compound and used as a raw material for synthesizing the maleimide compound, and further that the discoloration speed is considerably enhanced by the existence of a small amount of chlorine compounds contained in the maleimide compound.

Further, it has also been found that if a volatile organic solvent exists in a maleimide compound, the organic solvent in the maleimide compound evaporates from the surface of the solid maleimide compound during its storage and at the same time, the amines and chlorine compounds contained therein are concentrated on the solid surface, thereby causing the promotion of discoloration of the maleimide compound.

Furthermore, we have studied about how the extent of discoloring the maleimide compound is effected by each of the components, to find that a maleimide compound excellent in storage stability which is extremely hard to discolor can be obtained by controlling the content of each component within a specific range. Thus, the present invention has been completed.

BEST MODE FOR CARRYING OUT THE INVENTION

Specifically, the present invention is to provide a maleimide compound with improved storage stability wherein the content of primary amines is not more than 500 ppm. It is preferable that the content of chlorine compounds reduced as a chlorine atom is not more than 10 ppm or that the content of volatile components having a boiling point of not more than 200° C. at normal pressure is not more than 2,000 ppm. Further, the present invention is to provide a maleimide compound with improved storage stability wherein the content of the primary amines is not more than 500 ppm and the content of maleic anhydride is in the range of 5 to 2,000 ppm. Furthermore, the present invention is to provide a maleimide compound with improved storage stability wherein the content of the primary amines is not more than 500 ppm and the content of 2-amino-N-substituted succinimide compounds is not more than 300 ppm.

The present invention will be explained in more detail as follows. The maleimide compounds in accordance with the present invention include, for example, N-alkyl maleimides such as N-methyl maleimide, N-ethyl maleimide, N-hexyl maleimide, N-octyl maleimide and N-dodecyl maleimide; N-benzyl maleimides; N-cycloalkyl maleimides such as N-cyclohexyl maleimide; N-phenyl maleimides; N-substituted phenyl maleimides having a nitro group, an alkoxyl group, an alkyl group, a carboxyl group, a hydroxyl group or a halogen atom of N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide and N-tribromophenyl maleimide and the like substituted, but it should not be considered that the present invention is limited by these compounds. The present invention is especially effective when aromatic substituted maleimide compounds are used.

The essence of the present invention is that the content of primary amines in the maleimide compound is very low as mentioned above.

In order to improve the storage stability of the maleimide compound just mentioned above, it is necessary to control a content of the primary amines in the maleimide compound to a level of not more than 500 ppm, preferably in the range of 0.5 to 400 ppm, more preferably in the range of 1 to 300 ppm. Further, it is preferable to control a maleic anhydride content in the maleimide compound to a level in the range of 5 to 2,000 ppm, preferably 10 to 1,000 ppm, more preferably 20 to 400 ppm. Furthermore, it is preferable to control a content of 2-amino-N-substituted succinimide compounds in the maleimide compound to a level of not more than 300 ppm, preferably in the range of 0.5 to 200 ppm, more preferably in the range of 1 to 120 ppm.

Specifically, the discoloration of the maleimide compound can be suppressed within an allowable range by limiting the content of the primary amines, or the contents of the primary amines and maleic anhydride or 2-amino-N-substituted succinimide compounds to a level not exceeding the content just mentioned above. If the content of the primary amines, or the contents of the primary amines and maleic anhydride or 2-amino-N-substituted succinimide compounds exceed the above-mentioned values, it is not preferable because the discoloration of the maleimide compound increases remarkably.

In addition to the contents of the primary amines and 2-amino-N-substituted succinimide compounds, the discoloration of the maleimide compound can be prevented by decreasing a content of chlorine compounds therein reduced as a chlorine atom to a level of not more than 10 ppm, especially not more than 5 ppm. If the chlorine content is not more than 10 ppm, there is no problem, but if it exceeds the upper limit, the discoloration rate increases. Further, this chlorine compound is introduced as a very small amount of the chlorine compound from a catalyst, a solvent, a dehydrator, water or maleic anhydride as a raw material which are used for the production of the maleimide compound.

As these chlorine compounds, alkyl chlorine compounds such as chloroform and carbon tetrachloride, aromatic chlorine compounds such as chlorobenzene and dichlorobenzene, inorganic chlorine compounds such as zinc chloride, sodium chloride, hydrochloric acid and chlorosulfuric acid, and organic phosphate esters having a chlorinated alkyl group and a chlorinated aryl group such as tris(2-chloroethyl) phosphate, tris(dichloropropyl) phosphate, octyl dichloropropyl phosphate and phenyl dichloropropyl phosphate, organic acids such as trichloroacetic acid and sulfinyl chloride can be cited, for example.

Further, if volatile components are contained in a maleimide compound, the primary amines and chlorine compounds contained in the maleimide compound are locally concentrated with the evaporation of the volatile components. So a part of the maleimide compound in the storage container is likely to be influenced adversely, such as discolored remarkably. The volatile component used herein means a compound having a boiling point of not more than 200° C. at normal pressure. As the typical examples thereof, benzene, toluene, a petroleum fraction having a boiling point in the range of 50° to 120° C., xylenes, ethyl benzene, isopropyl benzene, cumene, mesitylene, tert-butyl benzene, pseudocumene, trimethyl hexane, octane, tetrachloroethane, nonane, chlorobenzene, ethyl cyclohexane, a petroleum fraction having a boiling point in the range of 120° to 170° C., m-dichlorobenzene, sec-butylbenzene, p-dichlorobenzene, decane, p-cymene, o-dichlorobenzene, butyl benzene, decahydronaphthalene, dimethyl formamide, dimethyl acetamide, and the like can be cited. The content of the volatile components in the maleimide compound is preferably suppressed to an amount of not more than 2,000 ppm, preferably not more than 1,000 ppm. If it exceeds 2,000 ppm, it is more likely to be influenced.

Further, when the maleimide compound is prepared from maleic anhydride and primary amines, various compounds are usually mixed in the final maleimide compound as impurities from raw materials or as byproducts of the reaction.

According to our knowledge, the content of the primary amines which are unreacted raw materials varies considerably depending on the manufacturing conditions of the maleimides. For example, if the reaction molar ratio of maleic anhydride and the primary amines as raw materials is approximately 1 or the amount of the primary amines is excessive, the primary amines are contained in the product in a large amount. Further, although a reaction liquid is washed with water in order to purify the maleimide compound produced by the maleimide synthesis reaction, the produced maleimide compound is sometimes hydrolyzed and produces the primary amines again which are raw materials. During the production of the maleimide compound, impurities by-produced from the primary amines as raw materials by reaction, purification and the like are sometimes decomposed with heat and the primary amines as raw materials are liberated again.

Further, the content of the 2-amino-N-substituted succinimide compound in the final maleimide compound varies considerably. For example, when the molar ratio of maleic anhydride and the primary amines is approximately 1 or the amount of the primary amines is excessive, the 2-amino-N-substituted succinimide compound in the product is contained in a large amount. Further, although a reaction liquid is washed with water in order to purify the maleimide compound produced by the maleimide synthesis reaction, the by-produced impurities are sometimes hydrolyzed to produce an 2-amino-N-substituted succinimide compound. In order to suppress the formation of the 2-amino-N-substituted succinimide compound, the reaction molar ratio of the maleic anhydride and the primary amines is adapted to be not less than 1 or the 2-amino-N-substituted succinimide compound is decomposed by the addition of maleic anhydride at a latter stage of the reaction.

The typical examples of the method for preparing maleimide compound in accordance with the-present invention will be described as follows:

(1) A method for imidation of maleinamic acids by heat dehydration in the presence of an acid catalyst using as a diluent a non-polar solvent such as toluene, xylene, and chlorobenzene or a mixture of a polar solvent such as dimethyl formamide, dimethyl sulfoxide, N-methyl pyrrolidone and sulforane with the non-polar solvent described above.

(2) A method for imidation of maleinamic acids by direct heat dehydration in the presence of an acid catalyst without using.

(3) A method for imidation of maleinamic acids by dehydration using a dehydrator such as acetic anhydride.

(4) A method for imidation of maleinamic acids by heat dehydration in the presence of an acid catalyst and a stabilizer using an organic solvent as a diluent.

The aforementioned maleinamic acids are obtained by adding and reacting maleic anhydride with primary amines. In this case, unreacted primary amines which are contained in maleinamic acids are introduced into reaction liquids of (1) to (4) described above. With any method described above, therefore, the amount of the residual primary amines mixed in the reaction liquid after the dehydration reaction of maleinamic acids is preferably as small as possible (preferably in the approximate range of 1 to 10,000 ppm). So, the reaction conditions for adding and reacting maleic anhydride with primary amines are advantageously adjusted so as that the unreacted primary amines are not present. For this purpose, it is preferable that maleinamic acids are produced with a molar ratio (M/A) of maleic anhydride (M) and primary amines (A) of not less than 1, for example. Even when the ratio of the reaction system is out of the aforementioned range, however, the primary amines, maleic anhydride and 2-amino-N-substituted succinimide compounds, for example, can be removed in the purification process after the aforementioned dehydration process described below, although the burden on the purification process would be large.

Then, the crude maleimide compound obtained by the aforementioned dehydration reaction is subjected to a purification process thereby purified. In this purification process, crystals of maleimide to be separated out from the reaction liquid are washed With water. Otherwise, the reaction liquid is washed with water in the intact form, and therefore primary amines, maleic anhydride, fumaric acid, maleinamic acids, and other water-soluble impurities to be contained in the reaction liquid are removed. In this treatment, the crude maleimide compounds are preferably dissolved in an organic solvent so that the treatment of washing with water can be more easily carried out. Organic solvents which can be preferably used herein include benzene, toluene, xylene, mesitylene, cumene, ethylbenzene, cymene, and chlorobenzene, for example. In this case, a polar solvent such as dimethylformamide, dimethyl sulfoxide, N-methyl pyrrolidone, and sulforane may be additionally contained therein. It is particularly preferable that the aforementioned organic solvents are used in the manufacturing process of the maleimide compound, because the reaction liquid can be washed with water while it is in the intact form.

In this process of washing the maleimide compound with water, because the maleimide compound is easily hydrolyzed by contact with water and primary amines are reproduced via maleinamic acids, it is necessary to pay particular attention to make the time of contact with water as short as possible. As one example, a treatment of continuously washing the maleimide compound with water which is effective and takes only a short time is recommended rather than a treatment which is carried out batchwisely. Specifically, an organic solvent layer which is a reaction liquid containing a maleimide compound is continuously contacted with an aqueous layer in an air column, a packed column, or a plate column at a temperature in the range of 20° to 90 ° C. for a time in the range of 0.1 second to 60 minutes, and the water-soluble components can, therefore, be effectively removed with the primary amines produced by the hydrolyzation repressed.

Then, the organic solvent is removed by heating from the reaction liquid which has been washed with water. In this case, primary amines are disadvantageously reproduced by heat-decomposition of the impurities contained in the crude maleimide compound. The exposure time of the maleimide compound to a high temperature, therefore, is preferably as short as possible. In this process of removing the solvent, the exposure time of the maleimide compound to a high temperature is shortened by carrying out the process of removing the solvent continuously rather than batchwisely, similar to that of washing with water. A liquid membrane downstream type condenser, or a thin membrane evaporator which fulfills the objects described above can be preferably used, for example.

As described above, the content of the primary amines is desirably as small as possible. In the present manufacturing technique and purification art of maleimide, however, it is economically disadvantageous when the content thereof is less than 1 ppm.

The reproduced primary amines are present in the various parts of the manufacturing process of maleimide compound. In order to prevent the contamination of amines as raw materials in the maleimide compound, each condition of the manufacturing process of the maleimide compound must be studied carefully, to set the conditions which prevent the reproduction of the primary amines as raw materials as far as possible.

In addition to setting the conditions of preventing the reproduction of the primary amines as raw materials as far as possible, notable improvement of the storage stability can be obtained by adjusting the content of the maleic anhydride so that the maleic anhydride in the product fulfills the specific condition. The amount of the maleic anhydride to be added in the product is necessarily adjusted to a level in the range of 5 to 2,000 ppm in the maleimide compound of the final product. If the content of the maleic anhydride is less than 5 ppm, the stability effected by the addition of maleic anhydride is unsatisfied. Conversely, it is undesirable to exceed 2,000 ppm, because of the adverse effects on quality such that the heat-resistance of the resin product produced with maleimide compound deteriorates, or silver streakings occur in the molded product. The maleic anhydride to be added for the adjustment of the amount of the maleic anhydride in the maleimide compound product can be added in any part of the manufacturing process of the maleimide compound. Preferably, it is added after washing with water, or in the process of obtaining a final product.

In addition to setting the conditions of preventing the reproduction of the primary amines as far as possible, notable improvement of the storage stability can be obtained by adjusting the content of the 2-amino-N-substituted succinimide compounds so as that the 2-amino-N-substituted succinimide compounds in the product fulfill the specific condition.

The 2-amino-N-substituted succinimide compound described herein has a structure of the formula as below.

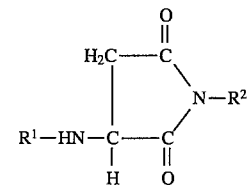

wherein $R^1$ and $R^2$ is an alkyl group having a number of carbon atoms in the range of 1 to 20; a cycloalkyl group; a phenyl group; a phenyl group substituted with a nitro group, an alkoxy group, a carboxyl group, a hydroxyl group, and a halogen atom, for example.

The amount of the 2-amino-N-substituted succinimide compounds to be contained in the product is necessarily adjusted to be in the range of 1 to 300 ppm in the maleimide compound of the final product. If the amount is more than 300 ppm, the discoloration of the maleimide compound during the storage is promoted. Although the reason thereof is not clear, it is considered that the primary amines are changed into color components by the interposition of the 2-amino-N-substituted succinimide compound. Further, the 2-amino-N-substituted succinimide compound is not preferable, because it has adverse effects on the quality of the product such that heat-resistance of the resin product produced with maleimide compound deteriorates, and silver streakings occur in the molded product. The content of the 2-amino-N-substituted succinimide compounds is preferably as small as possible. If it is less than 0.5 ppm, however, it is not economical because the cost for separating it from a maleimide compound is unduly high.

Chlorine compounds and volatile components which have the effect of promoting the production of color substances from primary amines, or primary amines and maleic anhydride or 2-amino-N-substituted succinimide compound must be mixed in the product of the maleimide compound in an amount as small as possible. When a chlorine type compound is needed for the production with a catalyst, a solvent, a dehydrator, water, and maleic anhydride as a raw material which are necessary for the synthesis of maleimide compound, for example, chlorine compounds are inevitably mixed therein. Compounds containing no chlorine compounds, therefore, must be used as raw materials in the production of maleimide compound.

As compounds which can be easily mixed during the synthesis of maleimide compound, and have important effects on the production of color components, compounds described below can be cited, for example. Specifically, chlorinated alkyl compounds such as chloroform and carbon tetrachloride, chlorinated aromatic hydrocarbons such as chlorobenzene and dichlorobenzene, inorganic chlorine compounds such as zinc chloride, sodium chloride, hydrochloric acid and chlorosulfuric acid, organic phosphate esters having a chlorinated alkyl group and a chlorinated aryl group such as tris(2-chloroethyl) phosphate, tris(dichloropropyl) phosphate, octyl dichloropropyl phosphate and phenyl dichloropropyl phosphate, chlorinated organic acids such as trichloroacetic acid, and chlorinated sulfinyls can be cited, for example.

Volatile components such as reaction solvents must be separated and removed as much as possible in the purification process of maleimide compound. In packing a maleimide compound into a product container, it is effective to ventilate a maleimide compound with an inert gas so as to minimize the content of the volatile components.

Maleimide compounds are generally obtained from maleic anhydride and primary amines by the reactions known to the art. According to the knowledge of the present inventors, maleimide compounds to be produced from the two raw materials described above contain primary amines as unreacted raw materials. From these primary amines, a colored substance is produced during the storage of the aforementioned maleimide compounds and is a cause of the discoloration of the maleimide compounds. When the amount of the primary amines to be contained in the maleimide compound is in the range of 1 to 500 ppm, discoloration is not notably shown. If the amount exceeds 500 ppm, the maleimide compound is unduly colored.

By adjusting the amount of the maleic anhydride in the maleimide compound to a level in the range of 5 to 2,000 ppm, the discoloration of the maleimide compound is satisfactorily repressed.

This discoloration is promoted by a small amount of chlorine compounds introduced from a catalyst, a solvent, a dehydrator, water or maleic anhydride as a raw material which are used for the production of the maleimide compound, for example. If the chlorine content is not more than 10 ppm, there are no problems (it is particularly preferable to be not more than 5 ppm). If it exceeds 10 ppm, the speed of the discoloration is unduly high.

When volatile components are contained in the maleimide compound, since primary amines and chlorine compounds which are contained in the maleimide compound are locally condensed with the evaporation of these volatile components, adverse effects such as the notable discoloration of a part of the maleimide compound in a storage container occur. The volatile components whose boiling point are not more than 200° C. at normal pressure are not particularly preferred. When the maleimide compound contains volatile components in an amount of more than 2,000 ppm, the adverse effects occur particularly easily.

The present invention will be described more specifically with working examples below.

The N-phenyl maleimides which are to be used in Examples and Controls were produced by the methods as following.

REFERENTIAL EXAMPLE 1

In an adjustable tank having a volume of 500 liters and provided with a stirrer, 200 kg of orthoxylene and 40 kg of orthophosphate were supplied and 60 kg of diatomaceous earth (trade name; Radiolite #200, produced by Showa Kagaku Kogyo Co., Ltd.) were added thereto, thereby depositing orthophosphate thereon. Then, 19 kg of aniline was added thereto, thereby converting a part of the phosphate to be deposited into amine salts.

In a reaction tank having a volume of 2 $m^3$ and provided with a thermometer, a condenser with a separation tank of water, and a stirrer, 110 kg of maleic anhydride and 100 kg of orthoxylene were placed and dissolved. Then, the temperature of the inside of the tank was adjusted to 80° C., and a solution of 100 kg of aniline dissolved in 600 kg of orthoxylene was added quantitatively over 30 minutes, thereby synthesizing an orthoxylene slurry of N-phenyl maleinamic acid.

To this slurry, the total amount of the aforementioned deposited catalyst and 0.2 kg of copper dibutyl dithiocarbamate were added, and the resultant mixture was heated. The temperature of the reaction tank was maintained at 140° C. while stirring. As the water to be produced with the reaction was removed with orthoxylene, the reaction was carried out over three hours, to produce N-phenyl maleimide. Thus, a reaction liquid (orthoxylene solution) containing N-phenyl maleimide was obtained.

The total raw materials to be used contained chlorine in a total amount of 0.4 g. In an apparatus for continuously washing with water provided with a linemixer (inside diameter of 13.5 mm, trade name; Skeyamixer, and produced by Sakura Seisakusho Co., Ltd.) and a packing column (having 200 mm of inside diameter, 2,000 mm of packing height, and pall ring having 1 inch of packing diameter), 300 kg/hr of the reaction liquid thus obtained was continuously contacted with 60 kg/hr of pure water in parallel flow at a temperature of 85° C. in the linemixer as a first stage, after separating a catalyst therefrom. Then, this mixed solution was introduced into the lower part of the packing column and separated. Thereafter, the reaction liquid which had ascended up was subjected to washing treatment with water as a second stage by being contacted with dispersed pure water at a rate of 60 kg/hr at a top of the column in an opposite flow direction.

After being washed with water, orthoxylene was removed from the reaction liquid under reduced pressure of 30 mmHg, and further vacuum distillation was carried out, to obtain 176 kg of yellow N-phenyl maleimide.

REFERENTIAL EXAMPLE 2

In a reaction tank having a volume of 2 $m^3$ and provided with a thermometer, a condenser with a separation tank of water, and a stirrer, 98 kg of maleic anhydride and 150 liters of toluene, 15 liters of dimethylsulfoxide and 3 kg of concentrated sulfuric acid were placed and dissolved by heat with stirring. The temperature of the liquid was maintained at a temperature of not less than 100° C.

Then, 93 kg of aniline was added to the mixed solution quantitatively over about 2 hours under reflux of the solvent, and thereafter aged for 2 hours at the same temperature.

Water which was produced during the addition and the aging was removed out of the system through the separation tank of water.

The total raw materials to be used contained chlorine in a total amount of 0.01 g. After the reaction was completed, a yellow and clear reaction liquid was washed batchwisely with 100 kg of pure water at 50° C. in one portion.

Then, the solvent was removed under reduced pressure of 50 mmHg and further vacuum distillation was carried out, to obtain 156 kg of yellow N-phenyl maleimide.

REFERENTIAL EXAMPLE 3

A reaction was carried out under the same conditions with the same apparatus as used in Referential Example 1, except that the total raw materials to be used contained chlorine in a total amount of 0.1 g. Thereafter, the reaction liquid thus obtained and 30 kg of pure water added thereto were subjected to washing treatment with water batchwisely at 85° C. in one portion. Xylene was removed under reduced pressure of 50 mmHg from the reaction liquid after being washed with water. Further, vacuum distillation was carried out, to obtain 177 kg of yellow N-phenyl maleimide.

REFERENTIAL EXAMPLE 4

A reaction was carried out under the same conditions with the same apparatus as used in Referential Example 2, except that the total raw materials to be used contained chlorine in a total amount of 0.01 g. The reaction liquid thus obtained and 100 kg of pure water added thereto were subjected to washing treatment with water batchwisely at 50° C. in one portion. The washed reaction liquid was cooled to a temperature of 30° C. to separate crystals and the crystals were filtered off. Then, the solvent was removed under reduced pressure of 50 mmHg from the reaction liquid. Thus, 158 kg of yellow N-phenyl maleimide was obtained.

REFERENTIAL EXAMPLE 5

A reaction was carried out under the same conditions with the same apparatus as used in Referential Example 1, except that the total raw materials to be used contained chlorine in a total amount of 2.5 g. The reaction liquid thus obtained and 60 kg of pure water added thereto were subjected to washing treatment with water batchwisely at 50° C. in one portion. The washed reaction liquid was cooled to a temperature of 30° C. to separate crystals and the crystals were filtered off. Then, xylene was removed under reduced pressure of 40 mmHg from the reaction liquid. Thus, 179 kg of yellow N-phenyl maleimide was obtained.

EXAMPLES 1 TO 2, AND CONTROLS 1 TO 3

100 kg of N-phenyl maleimide to be prepared by the methods as described above and having a shape and impurity composition as shown in Table 1 was packed hermetically in a drum made of stainless steel with 59 cm in diameter and 89 cm in height and kept in a room. The storage temperature was maintained at a temperature in the range of 10° to 40° C., and direct sun light was avoided. The storage time was one year and each N-phenyl maleimide was taken out of the drum every three months and its appearance was observed. Results as shown in Table 1 were obtained.

TABLE 1

| Variation of time of N-phenyl maleimide | | | Example 1 | Example 2 | Control 1 | Control 2 | Control 3 |
|---|---|---|---|---|---|---|---|
| Shape | | | Flaky | Flaky | Flaky | Flaky | Flaky |
| Composition | Purity | (wt %) | not less than 99.5 | not less than 99.5 | not less than 99.5 | 99.0 | 99.0 |
| | Aniline | (ppm) | 10 | 320 | 760 | 980 | 880 |
| | Maleic anhydride | (ppm) | 50 | 380 | 50 | 100 | 200 |
| | 2-Anilino-N-phenyl succinimide | (ppm) | 80 | 80 | 80 | 650 | 600 |
| | Chlorine | (ppm) | 2 | not more than 0.1 | 0.5 | not more than 0.1 | 12 |
| Volatile component | | | Xylene | Toluene  Dimethyl sulfoxide | Xylene | Toluene  Dimethyl sulfoxide | Xylene |
| | Amount | (ppm) | 1000 | 300  1000 | 4000 | 400  870 | 2700 |
| Change of appearance | Before storage | | Bright yellow | Bright yellow | Bright yellow | Yellow | Yellow |
| | After 3 months | | Bright yellow | Bright yellow | Dull yellow | Dull yellow | Yellowish brown |
| | After 6 months | | Bright yellow | Bright yellow | Bluish black at upper part of drum | Yellowish brown totally therein | Yellowish brown totally therein Particularly the color of the upper part was strong |
| | After 9 months | | Bright yellow | Bright yellow | Bluish black at upper part of drum | Yellowish brown totally therein | Brownish at upper part of drum Particularly the color of the upper part was strong |
| | After 12 months | | Bright yellow | Bright yellow | Bluish black at upper part of drum | Yellowish brown totally therein | Brownish at upper part of drum Particularly the color of the upper part was strong |
| Remarks | Purity after 12 Purity (wt %) | | not less than 99.5 | not less than 99.5 | not less than 99.5 | 99.0 | 99.0 |

EXAMPLE 3

100 g of N-phenyl maleimide having a shape and impurity composition as shown in Table 2 was placed hermetically in a clear container made of polyethylene with 9.5 cm in length and 6.0 cm in width. The N-phenyl maleimide thus packed was stored in a room at a temperature in the range of 10° to 40 ° C. with direct sun light avoided. During the storage, each appearance was observed visually.

TABLE 2

| | | | Example 3 | Control 4 |
|---|---|---|---|---|
| Shape | | | Powdery (Average particle diameter 200 μm) | Powdery (Average particle diameter 200 μm) |
| Composition | Purity | (wt %) | not less than 99.5 | not less than 99.5 |
| | Aniline | (ppm) | 250 | 640 |
| | Chlorine | (ppm) | not more than 0.1 | not more than 0.1 |
| | Xylene | (ppm) | 870 | 3200 |
| Change of appearance | Before storage | | Bright yellow | Bright yellow |
| | After 6 months | | Bright yellow | Brownish at upper part Dull yellow totally therein |
| | After 12 months | | Bright yellow | Dull yellow totally therein |

CONTROL 5

A reaction was carried out under the same conditions with the same apparatus as used in Referential Example 2. The reaction liquid thus obtained was not subjected to washing treatment with water. A solvent was removed under reduced pressure of 200 mmHg and further, vacuum distillation was carried out, to obtain 158 kg of yellow N-phenyl maleimide.

N-phenyl maleimide thus obtained was tested by the same method as used in Example 3, to obtain results as shown in Table 3.

TABLE 3

| Shape | | | Flaky | |
|---|---|---|---|---|
| Composition | Purity | (wt %) | 98.5 | |
| | Aniline | (ppm) | 1,000 | |
| | Chlorine | (ppm) | not more than 0.1 | |
| | Volatile component | (ppm) | Toluene Dimethyl sulfoxide | 1,000 5,000 |
| Change appearance | Before storage | | Yellow | |
| | After 3 months | | Bluish black at upper part of drum Yellowish brown totally therein | |
| | After 6 months | | Brownish at upper part of drum | |
| | After 12 months | | Brownish totally therein | |
| Remarks | Purity after 12 months | (wt %) | 98.5 | |

EXAMPLE 4 AND CONTROL 6

100 g of N-phenyl maleimide having a shape and impurity composition as shown in Table 4 was packed hermetically in a clear container made of polyethylene with 9.5 cm in length and 6.0 cm in width. The N-phenyl maleimide thus packed was stored in a room at a temperature in the range of 10° to 40° C. with direct sun light avoided. During the storage, each appearance was observed visually.

TABLE 4

| | | | Example 4 | Control 6 |
|---|---|---|---|---|
| Shape | | | Powdery (Average particle diameter 200 μm) | Powdery (Average particle diameter 200 μm) |
| Composition | Purity | (wt %) | not less than 99.5 | not less than 99.5 |
| | Aniline | (ppm) | 200 | 870 |
| | Maleic anhydride | (ppm) | 420 | 20 |
| | 2-Aniline-N-phenyl succinimide | (ppm) | 30 | 350 |
| | Chlorine | (ppm) | not more than 0.1 | not more than 0.1 |
| | Xylene | (ppm) | 530 | 4600 |
| Change of appearance | Before storage | | Bright yellow | Bright yellow |
| | After 6 months | | Bright yellow | Brownish at upper half Dull yellow at lower half |
| | After 12 months | | Bright yellow | Brownish at upper half Dull yellow at lower half |

INDUSTRIAL APPLICABILITY

As described above, the maleimide compound in accordance with the present invention is produced so that the content of primary amines or the contents of the primary amines and maleic anhydride or 2-amino-N-substituted succinimide compounds are controlled to a level not exceeding a specific amount and more preferably that the contents of chlorine compounds and volatile components are controlled to a level not exceeding a specific amount. It, therefore, shows remarkable storage stability. Such maleimide compound with improved storage stability is highly stable during its transportation and storage, so it does not cause a discoloration in a thermoplastic resin product which is the final product.

What is claimed:

1. A maleimide composition with reduced vulnerability to discoloration comprising
    a) 99.5 % by weight or more of maleimide selected from the group consisting of N-alkyl maleimides, N-benzyl maleimides, N-cycloalkyl maleimides, N-phenyl maleimides, and N-substituted phenyl maleimides;
    b) primary amine compounds at a level not exceeding 500 ppm; and
    c) chlorine compounds selected from the group consisting of alkyl chlorine compounds, aromatic chlorine compounds, inorganic chlorine compounds, organic phosphate esters having a chlorinated alkyl group and a chlorinated aryl group, and organic acids, said chlorine compounds being present at a level not exceeding 10 ppm as chlorine atoms in said maleimide composition.

2. The maleimide composition of claim 1 further comprising
    d) volatile compounds, which have a boiling point of not more than 200° C., at a level not exceeding 2,000 ppm;
    e) maleic anhydride at a level not exceeding 5 to 2000 ppm; and
    f) 2-amino-N-substituted succinimide compounds at a level not exceeding 300 ppm.

3. The maleimide composition of claim 1 wherein said maleimide is in a solid state.

4. The maleimide composition of claim 1 wherein said maleimide is an N-substituted phenyl maleimide.

5. A process of suppressing discoloration of maleimide compositions comprising 99.5% by weight or more of maleimide, said process comprising
   a) limiting the content of primary amines in said composition to a level not exceeding 500 ppm;
   b) limiting the content of chlorine compounds in said composition to a level not exceeding 10 ppm;
   c) limiting the content of volatile compounds in said composition to a level not exceeding 2,000 ppm;
   d) limiting the content of maleic anhydride in said composition to a level not exceeding 500 ppm; and
   e) limiting the content of 2-amino-N-substituted succinimide compounds to a level of not more than 300 ppm.

6. A process of suppressing the level of 2-amino-N-substituted succinimide compound in the maleimide composition of claim 5 comprising reacting maleic anhydride and primary amine in a molar ratio of not less than 1 in order to suppress formation of 2-amino-N-substituted succinimide compound.

7. The process of claim 5 wherein limiting the content of volatile compounds is performed by ventilating solid maleimide compound with an inert gas.

* * * * *